US011013958B2

(12) United States Patent
Bastide et al.

(10) Patent No.: US 11,013,958 B2
(45) Date of Patent: May 25, 2021

(54) PERFORMANCE OF FITNESS APPLICATION BASED ON FITNESS ACTIVITIES

(71) Applicant: International Business Machines Corporation, Armonk, NY (US)

(72) Inventors: Paul R. Bastide, Boxford, MA (US); Fang Lu, Billerica, MA (US); Ishwarya Rajendrababu, Hoboken, NJ (US); Mikaela Falk, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 376 days.

(21) Appl. No.: 15/900,908

(22) Filed: Feb. 21, 2018

(65) Prior Publication Data

US 2019/0255384 A1    Aug. 22, 2019

(51) Int. Cl.
*A63B 24/00* (2006.01)
*A61B 5/11* (2006.01)

(52) U.S. Cl.
CPC ........ *A63B 24/0062* (2013.01); *A61B 5/1118* (2013.01); *A63B 2024/0065* (2013.01); *A63B 2225/50* (2013.01)

(58) Field of Classification Search
CPC . A63B 24/0062; A63B 2225/50; A63B 24/00; A61B 5/1118; A61B 5/11
See application file for complete search history.

(56) References Cited

U.S. PATENT DOCUMENTS

| 2013/0218309 A1 | 8/2013 | Napolitano |
| 2017/0238881 A1 | 8/2017 | Cheng et al. |
| 2017/0329934 A1 | 11/2017 | Orenstein et al. |

FOREIGN PATENT DOCUMENTS

WO    2016049090 A2    3/2016

OTHER PUBLICATIONS

Hughes, "The 15 Next Big Fitness Trends", http://www.shape.com/fitness/trends/15-next-big-fitness-trends, Meredith Corporation, 2017, 29 pages.
Patel, "20 of the Best Free Online Workout Video Series", http://www.huffingtonpost.ca/2015/03/20/free-online-workout_n_6896426.html, The Huffington Post Canada, Mar. 20, 2015, 3 pages.
Smith, "The 50 Best Free Workout Resources You Can Find Online", http://www.huffingtonpost.com/dave-smith2/free-online-workout_b_7722024.html, Jul. 6, 2015, 13 pages.

*Primary Examiner* — Timothy A Musselman
(74) *Attorney, Agent, or Firm* — Edell, Shapiro & Finnan, LLC (57) ABSTRACT

A method, a system, and a computer program product are provided. A computing device receives information regarding one or more types of fitness activities. The computing device identifies respective fitness applications for monitoring each of the one or more fitness activities and installs the identified respective fitness applications on a user device to monitor user performance of a corresponding fitness activity.

20 Claims, 10 Drawing Sheets

PERFORMANCE OF FITNESS APPLICATION BASED ON FITNESS ACTIVITIES

BACKGROUND

1. Technical Field

Present invention embodiments relate to a method, a system and a computer program product for receiving information pertaining to at least one type of fitness activity, identifying a fitness application for monitoring each of the at least one type of fitness activity, and installing the identified fitness application for each of the at least one type of fitness activity on a user computing device to monitor user performance of corresponding fitness activities.

2. Discussion of the Related Art

A number of different fitness applications exist for tracking different fitness activities. The fitness applications may execute on portable devices including, but not limited to, wearable fitness trackers and handheld portable computing devices such as, for example, a smartphone. A fitness application may not always satisfy a user's requirements and/or may not always motivate a user to work out. As a result, a user may stop using the fitness application at some point. For example, a user may use a fitness application that only keeps track of exercises that are relevant to running. However, the user may love dancing, but not running. Therefore, the user's activity level may not be accurately reflected by the fitness application and a user's portable device may not provide any motivation to the user to exercise.

Busy schedules and/or financial considerations keep many people from going to a gym or a workout class. A growing number of people are fitting less traditional forms of exercise into their schedules aided by free online videos, guides and audiotapes. Some people will be unable to follow a specific fitness routine due to inclement weather or injuries and instead, may engage in multiple fitness routines over a period of time. However, people may be unable to measure their individual exercise progress using these less traditional forms of exercise.

SUMMARY

According to embodiments of the present invention, a method, a system and a computer program product are provided. At least one computing device receives information pertaining to at least one type of fitness activity. Respective fitness applications for monitoring each of the at least one type of fitness activity are identified. The respective identified fitness applications are installed on a user device to monitor user performance of a corresponding fitness activity.

BRIEF DESCRIPTION OF THE DRAWINGS

Generally, like reference numerals in the various figures are utilized to designate like components.

DETAILED DESCRIPTION

According to various embodiments of the invention, a method, a system, and a computer program product are provided for monitoring information exchanged on social networking websites and determining a ranking of fitness activities based on how frequently the fitness activities are mentioned on the social networking websites. Some embodiments may categorize fitness activities and tag them based on characteristics of the fitness activities. For example, the tags may include, but not be limited to, intensive, moderate, light, dance, jog, yoga and dance exercise. Embodiments may search for fitness applications that can effectively measure top ranked fitness activities and may suggest that found fitness applications be installed on a user's device. If a number of the found fitness applications for measuring a fitness activity is less than a threshold, embodiments may promote development of fitness applications to effectively measure the fitness activity.

Figure 1:
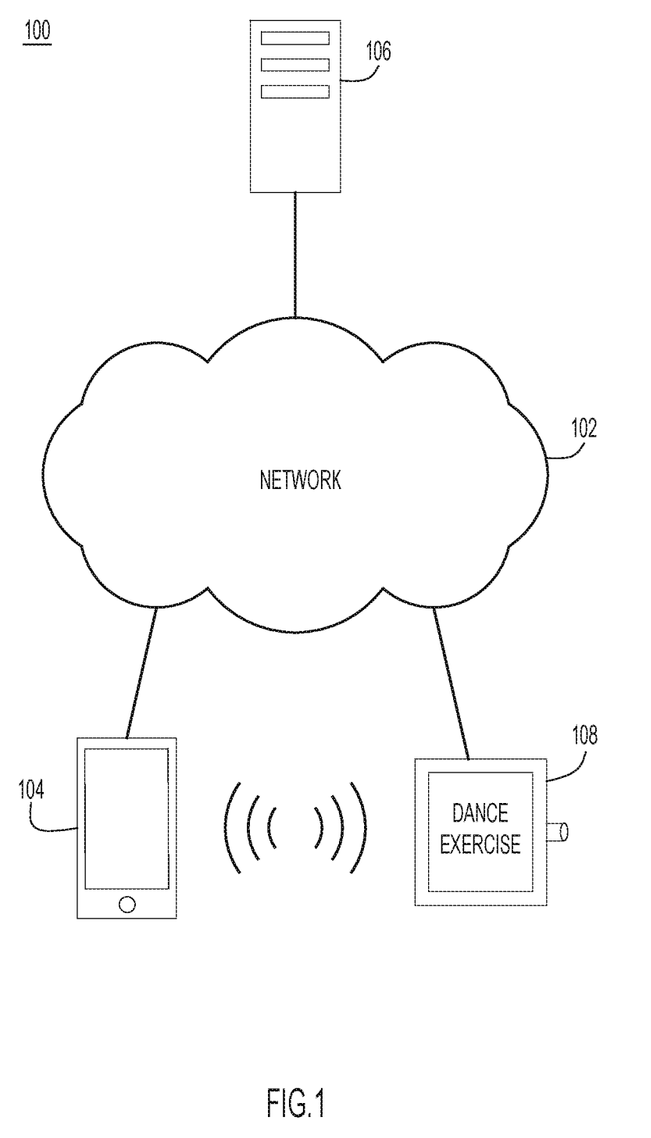
FIG. 1 shows an example environment in which embodiments of the invention may operate.

An example environment 100 for use with present invention embodiments is illustrated in FIG. 1. Specifically, environment 100 may include a network 102, a handheld portable device 104 wirelessly connected to network 102, a server 106 connected to network 102, and a wearable fitness tracking device 108 that may be wirelessly connected to handheld portable device 104.

Network 102 may be implemented by any number of any suitable communications media (e.g., wide area network (WAN), local area network (LAN), Internet, Intranet, public switched data network (PSDN), public switched telephone network (PSTN), etc.).

Handheld portable device 104 may communicate with server 106 via a wireless connection and network 102. The wireless connection may include a Wireless Fidelity (Wi-Fi) connection or other type of wireless connection. In some embodiments, handheld portable device 104 may include a smartphone.

Wearable fitness tracking device 108 may execute one or more fitness applications and may wirelessly communicate with handheld portable device 104. In some embodiments, wearable fitness tracking device 108 may communicate with handheld portable device 104 via Bluetooth® (Bluetooth is a registered trademark of Bluetooth Sig, Inc. Corp., incorporated in Delaware), or other wireless technology.

A first alternative environment may not include wearable fitness tracking device 108. Instead, handheld portable device 104 may execute one or more fitness applications and may communicate with server 106 via network 102 as previously described. A second alternative environment may include fitness tracking device 108, but may not include handheld portable device 104. In this alternative environment, fitness tracking device 108 may wirelessly communicate with network 102 using Wi-Fi or other wireless technology, and with server 106 via network 102.

Figure 2:
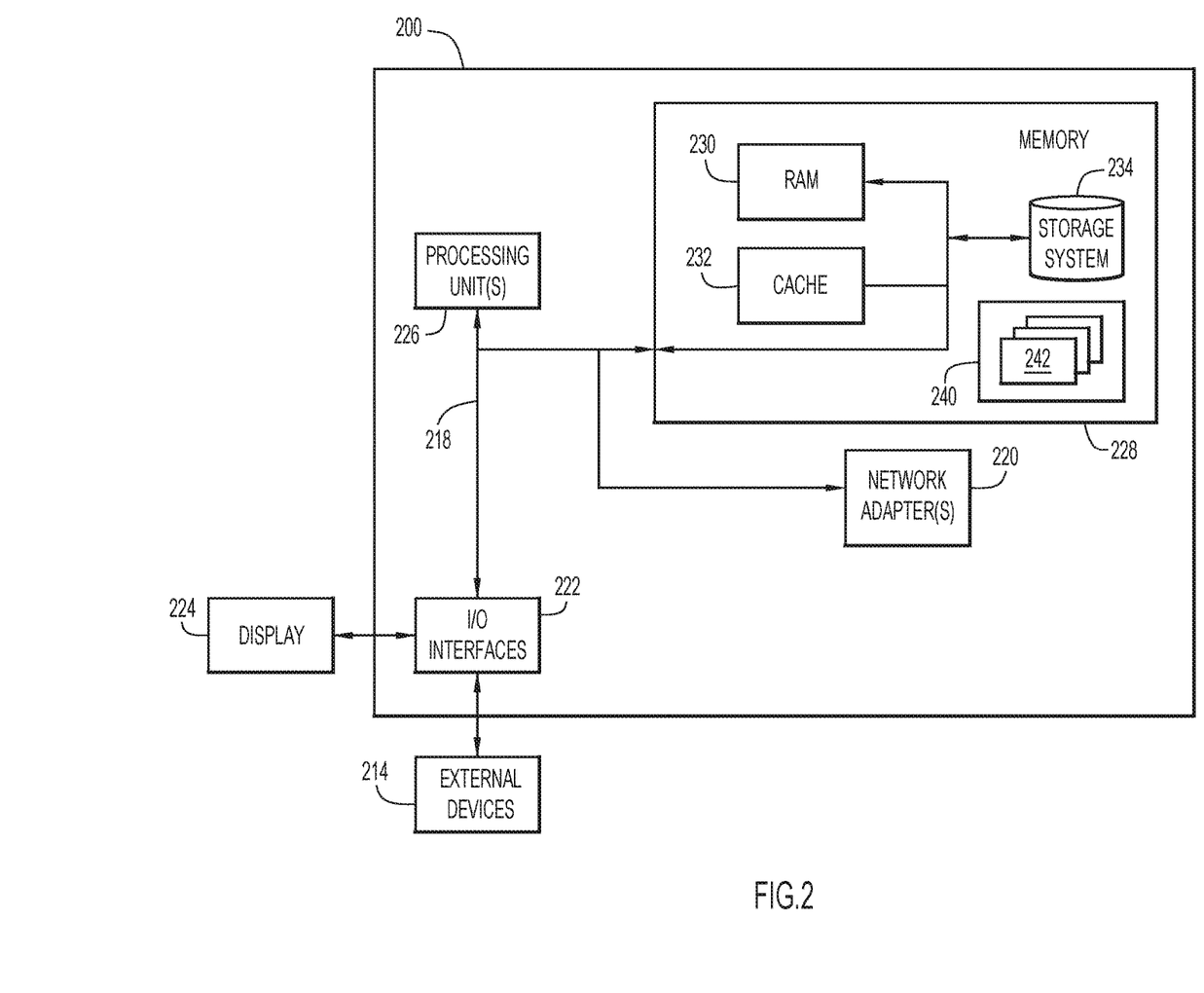
FIG. 2 is a functional block diagram of a computing system that may be used to implement embodiments of the invention.

FIG. 2 is a functional block diagram of a computing system 200 that may implement server 106, handheld portable device 104 and fitness tracking device 108 in various embodiments of the invention. Computing system 200 is shown in a form of a general-purpose computing device. Components of computing system 200 may include, but are not limited to, one or more processors or processing units 226, a system memory 228, and a bus 218 that couples various system components including system memory 228 to one or more processing units 226.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 typically includes a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, one or more displays 224, one or more devices that enable a user to interact with computing system 200, and/or any devices (e.g., network card, modem, etc.) that enable computing system 200 to communicate with one or more other computing devices. Such communication can occur via Input/Output (I/O) interfaces 222. Still yet, computing system 200 can communicate with one or more networks such as a local area network (LAN), a general wide area network (WAN), and/or a public network (e.g., the Internet) via network adapter 220. As depicted, network adapter 220 communicates with the other components of computing system 200 via bus 218. It should be understood that, although not shown, other hardware and/or software components could be used in conjunction with computing system 200. Examples, include, but are not limited to: microcode, device drivers, redundant processing units, external disk drive arrays, RAID systems, tape drives, and data archival storage systems, etc.

In the following embodiments, the term "user's device" may refer to handheld portable device 104, wearable fitness tracking device 108, or a combination of handheld portable device 104 and wearable fitness tracking device 108.

Figure 3:
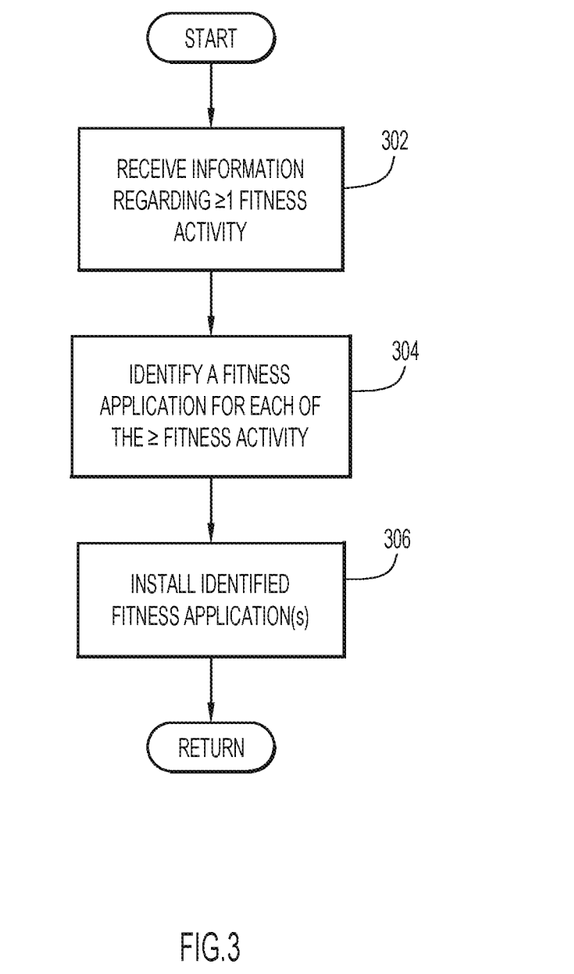
FIG. 3 is a flowchart of an example process for identifying and installing one or more fitness applications on a user device according to an embodiment of the present invention.

FIG. 3 is a flowchart illustrating an example process that may be performed according to some embodiments of the invention. The process may begin with server 106 receiving information regarding one or more fitness activities (act 302). In some embodiments, server 106 may monitor one or more social networks for any mention of fitness activities. In a variation of act 302, a user may provide a web address of a fitness video via a user interface of a user's device, which may then be provided to server 106. Upon receiving the web address during act 302, server 106 may analyze content of the web address such as, for example, a title and tags to determine a fitness activity associated with the video.

Server 106 may then identify a fitness application for each of the mentioned one or more fitness activities (act 304) by, for example, searching websites of known fitness application developers and/or websites of known fitness application sellers. Server 106 may then install the one or more identified fitness applications on a user's device, assuming that the user has given permission for the installation of the one or more identified fitness applications (act 306). The process may then complete.

Figure 4:
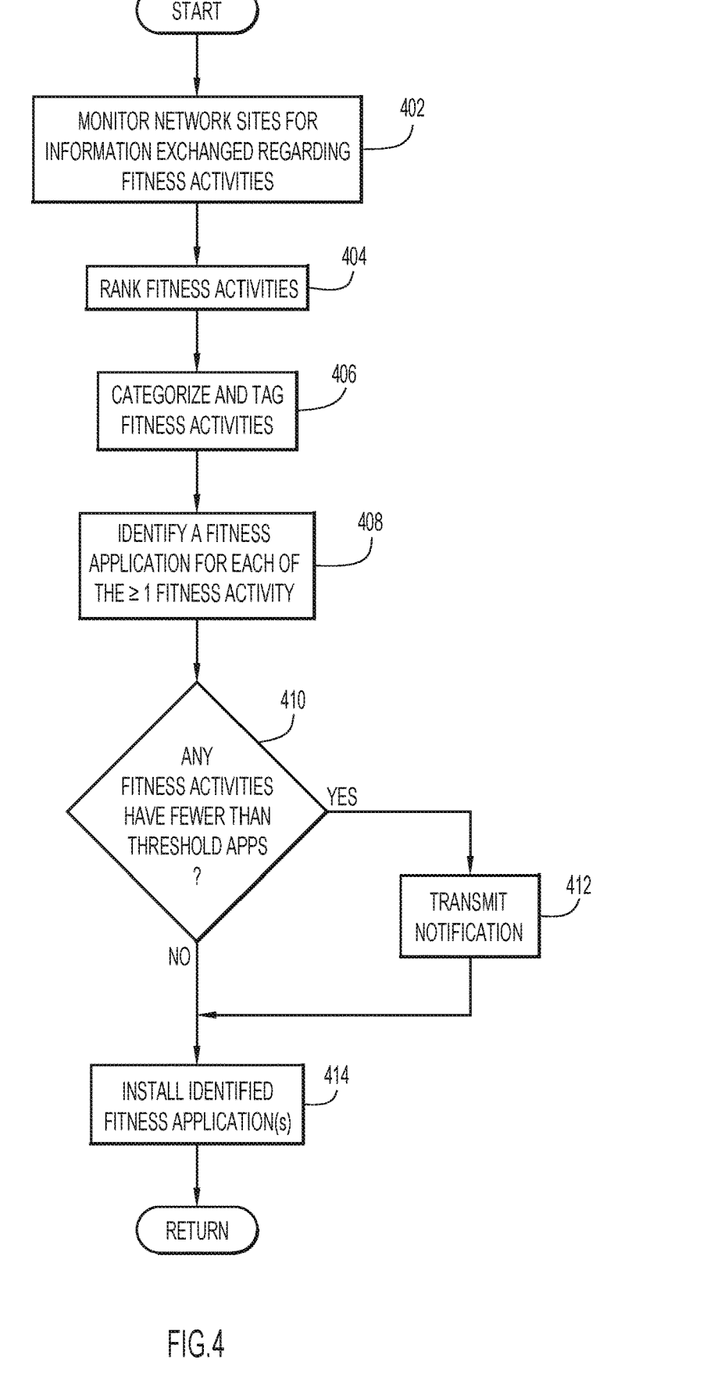
FIG. 4 is a flowchart of an example process in a variation of the embodiment of FIG. 3.

FIG. 4 is a flowchart that illustrates another example process that may be performed according to some embodiments of the invention for monitoring network sites for information exchanges regarding fitness activities, ranking the fitness activities, installing identified fitness applications for monitoring the fitness applications, and notifying fitness application developers to suggest development of applications to monitor fitness activities having fewer than a threshold number of identified fitness applications. The process may begin with server 106 monitoring network sites such as, for example, social networking sites, for any information exchanged regarding fitness activities (act 402). Server 106 may then rank the fitness activities based on a frequency at which each of the fitness activities is mentioned in information exchanges (act 404).

Server 106 may then categorize and tag each of the multiple fitness activities (act 406). Tags may be based on characteristics of fitness activities and may include, but not be limited to, intensive, moderate, light, dance, jog, yoga and dance exercise. A table of tags and corresponding fitness activities may be included in memory or a storage device accessible to server 106. Server 106 may then identify a fitness application for each of the one or more fitness activities (act 408) by searching known fitness application developer or seller websites. If any respective fitness activity of the one or more identified fitness activities has fewer than a threshold number of identified fitness applications for monitoring the respective fitness activity (act 410), then a notification may be sent by server 106 to one or more application developer websites, including but not limited to open-source application developer websites, suggesting development of a fitness application to monitor the respective fitness activity (act 412). If none of the identified one or more fitness activities have fewer than the threshold number of identified fitness applications for monitoring the respective fitness activity, or after performing act 412, server 106 may install the identified fitness application for each of the one or more fitness activities on a user's device, assuming that the user has given permission for installation of the respective fitness application (act 414).

In some embodiments, when performing act 408, server 106 may identify a fitness application for each of a top ranked number of fitness activities. The top ranked number may be 3, 10, or another suitable number. Thus, for example, if 3 is the top ranked number in an embodiment, then server 106 may identify a fitness application for each of a top 3 ranked fitness activities. The process may then install, on the user's device, a fitness application to measure each of the top ranked number of fitness activities, assuming the user has given permission for the installation, and may notify the one or more application developer websites regarding each of the top ranked number of fitness activities that have fewer than the threshold number of identified fitness applications.

Figure 5:
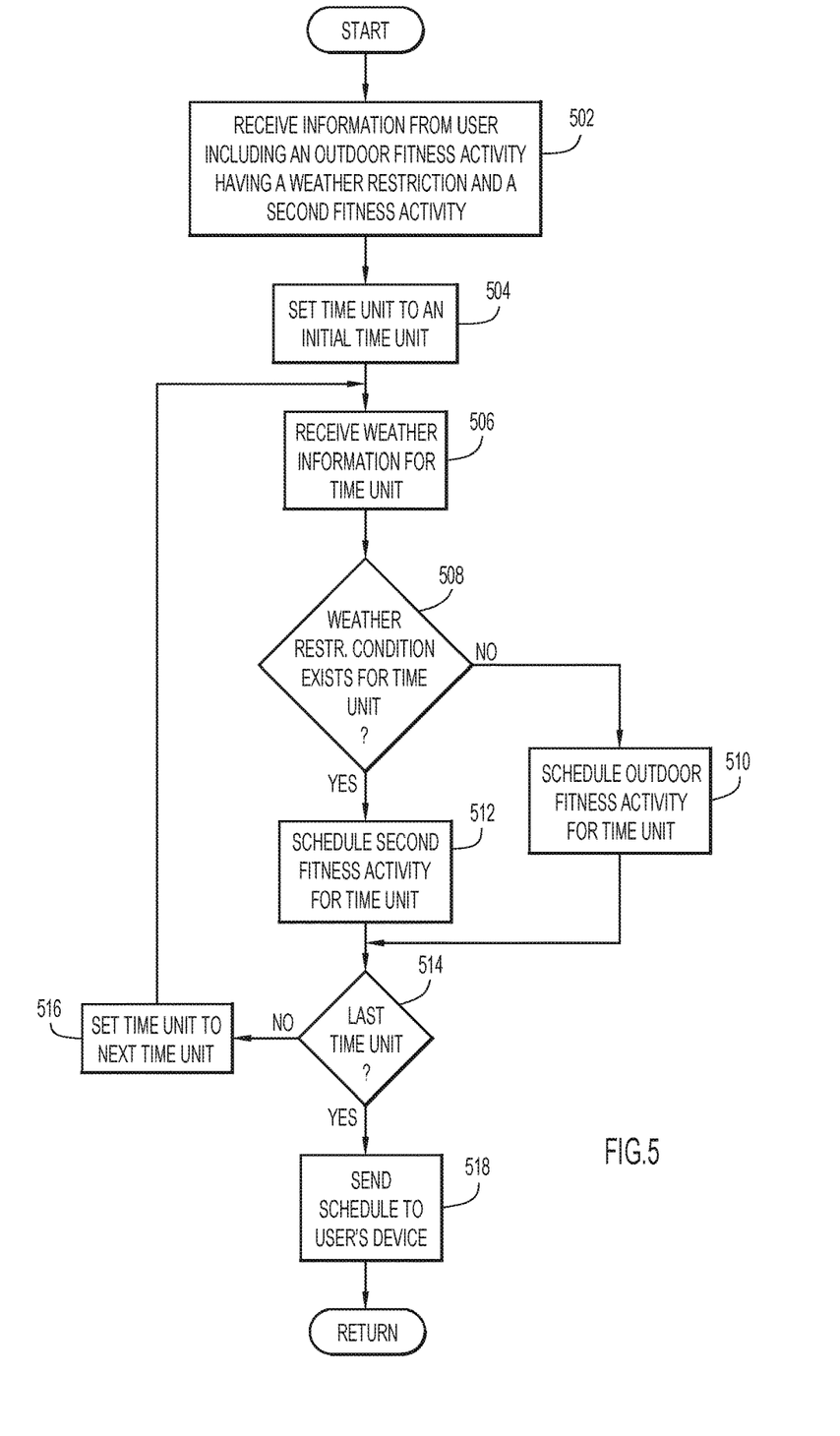
FIG. 5 is a flowchart of an example process for scheduling either an outdoor activity or a second activity to be monitored by a user device in accordance with a schedule according to an embodiment of the present invention.

FIG. 5 shows a flowchart of an example process that may be performed in some embodiments for creating a schedule of fitness activities for a user's device to monitor. The process may begin with server 106 receiving information provided from the user, via the user device, including an outdoor fitness activity that may be restricted by weather conditions, a corresponding location of the user, a second fitness activity, a starting date, an ending date and a time of day for a fitness activity (act 502). As an example, the received information may include information indicating bicycling as the outdoor fitness activity, rain or snow as the weather restriction condition, weightlifting as the second activity, 7 AM-8 AM as the time of day, May 1 as the starting date and May 15 as the ending date. Server 106 may then set a time unit to an initial time unit (act 504), which would be May 1, 7 AM-8 AM for the above example.

Server 106 may then obtain local weather information, with respect to the user, for the time unit (act 506) and may determine whether a weather restriction condition exists for the time unit (act 508). If the weather restriction condition exists (rain or snow for this example), then server 106 may schedule the second fitness activity (weightlifting for this example) for the time unit (act 512). If, during act 508, server 106 determines that the weather restriction condition does not exist for the time unit, then server 106 may schedule the outdoor fitness activity (bicycling for this example) for the time unit.

Server 106 may then determine whether the time unit is a last time unit (May 15, 7 AM-8 AM for this example) (act 514). If server 106 determines that the time unit is not the last time unit, then server 106 may set the time unit to a next time unit (May 2, 7 AM-8 AM for this example) (act 516). Server 106 may then repeat acts 506-514.

If, during act 514, server 106 determines that the time unit is the last time unit, then server 106 may provide the schedule to the user's device (act 518). The user's device may then execute a corresponding fitness application at the scheduled time unit to track the scheduled fitness activity. The example process of FIG. 5 assumes that the user's device already has fitness applications installed to monitor the specified fitness activities. In embodiments in which the user's device may not already have such fitness applications installed, server 106 may install the fitness applications in a same manner as described with respect to acts 304-306 (FIG. 3) and acts 408 and 414 (FIG. 4), assuming that the user has provided permission for the installation of the fitness applications.

In some embodiments, the user's device may periodically request server 106 to provide an update regarding at least some of the specified time units and the specified weather restriction condition. Upon receiving the request, server 106 may check latest weather conditions for the specified time units and may determine whether any of the weather conditions changed. If any of the weather conditions changed, server 106 may send an updated schedule of fitness activities to the user's device. The user's device may then execute a corresponding fitness application at the scheduled time unit to track the scheduled fitness activity according to the updated schedule.

Figure 6:
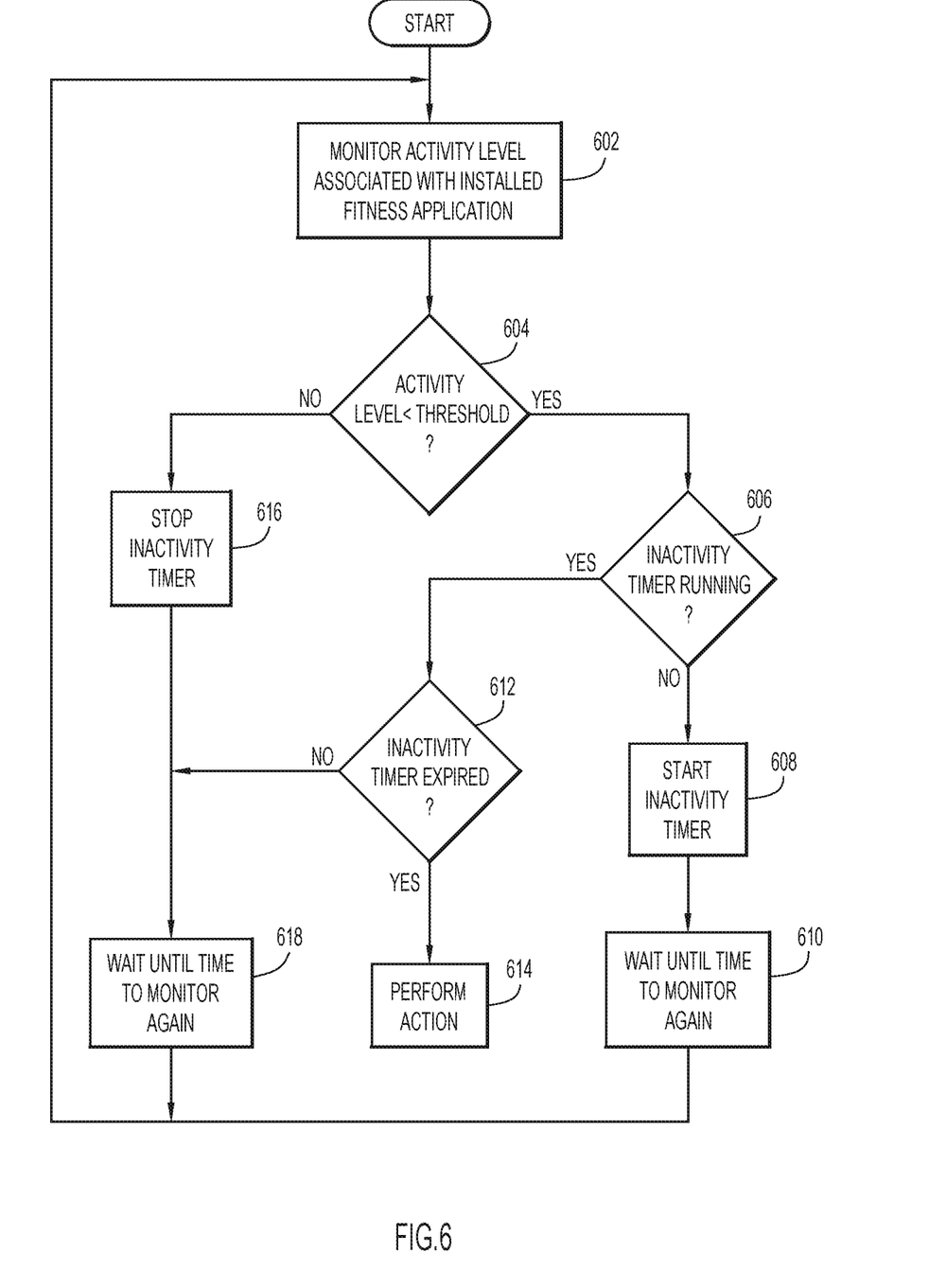
FIG. 6 is a flowchart of an example process for a user device to monitor an activity level associated with an installed fitness application and to perform an action when the activity level is determined to be below a threshold for at least a given period of time according to an embodiment of the present invention.

In various embodiments of the invention, the user's device may monitor an activity level associated with installed fitness applications and may perform some action if the activity level is below a threshold for at least a given time period. FIG. 6 is an example process that may be performed in such embodiments. The process may begin with the user's device monitoring an activity level associated with an installed fitness application (act 602). and determining whether the activity level is below a threshold for a given period of time (act 604). As an example, the threshold may be no use of the application for at least a one week period of time. Of course, other threshold values may be used in these embodiments.

If the activity level is determined to be below the threshold, then the user's device may determine whether an inactivity timer is running with respect to the fitness application (act 606). If the inactivity timer is determined not to be running with respect to the fitness application, then the user's device may start the inactivity timer (act 608) and may wait an amount of time before monitoring the activity level again (act 610).

Figure 7:
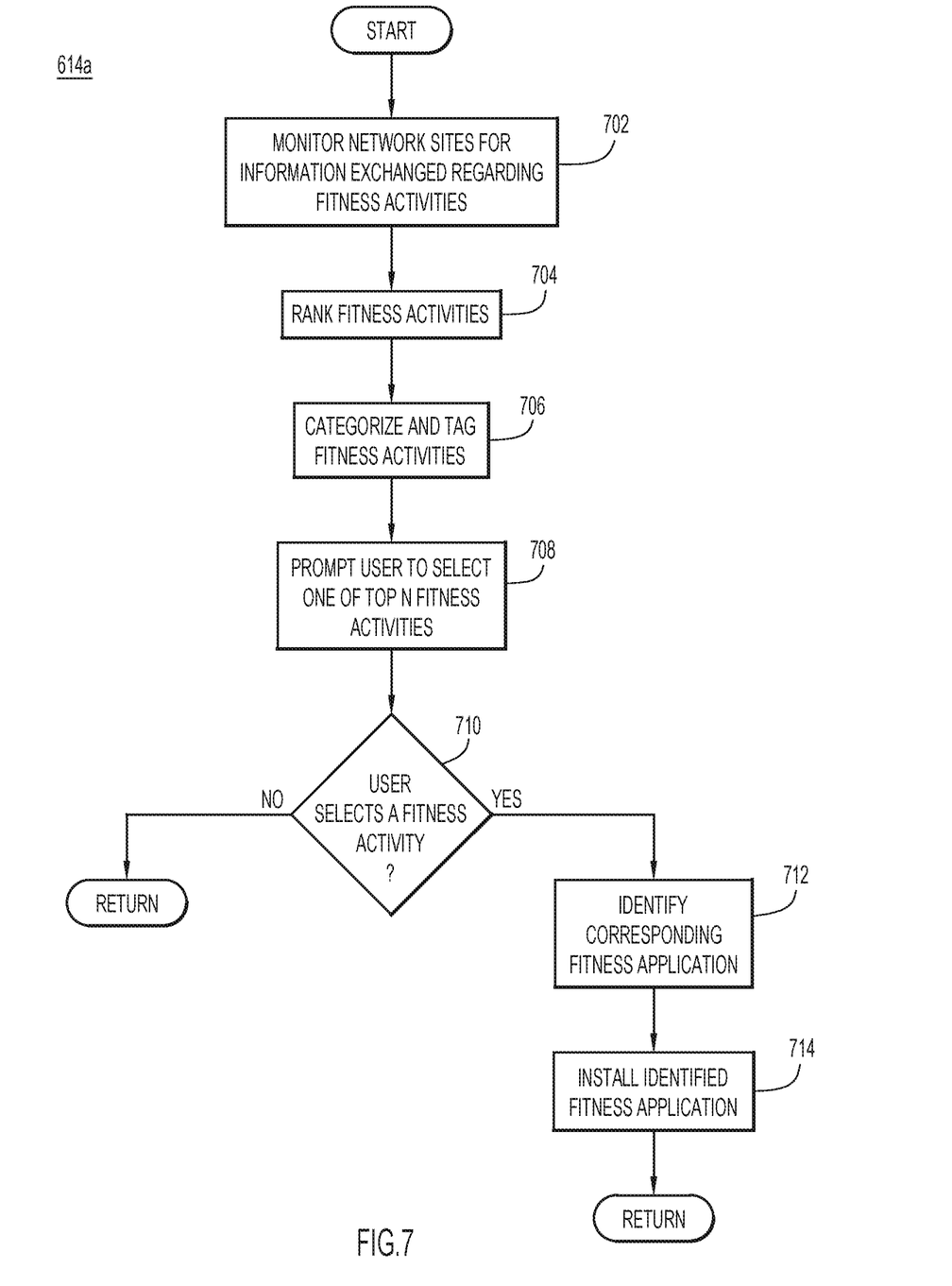
FIG. 7 is a flowchart of an example process for performing the action for inactivity indicated in the flowchart of FIG. 6 according to an embodiment of the invention.
Figure 8:
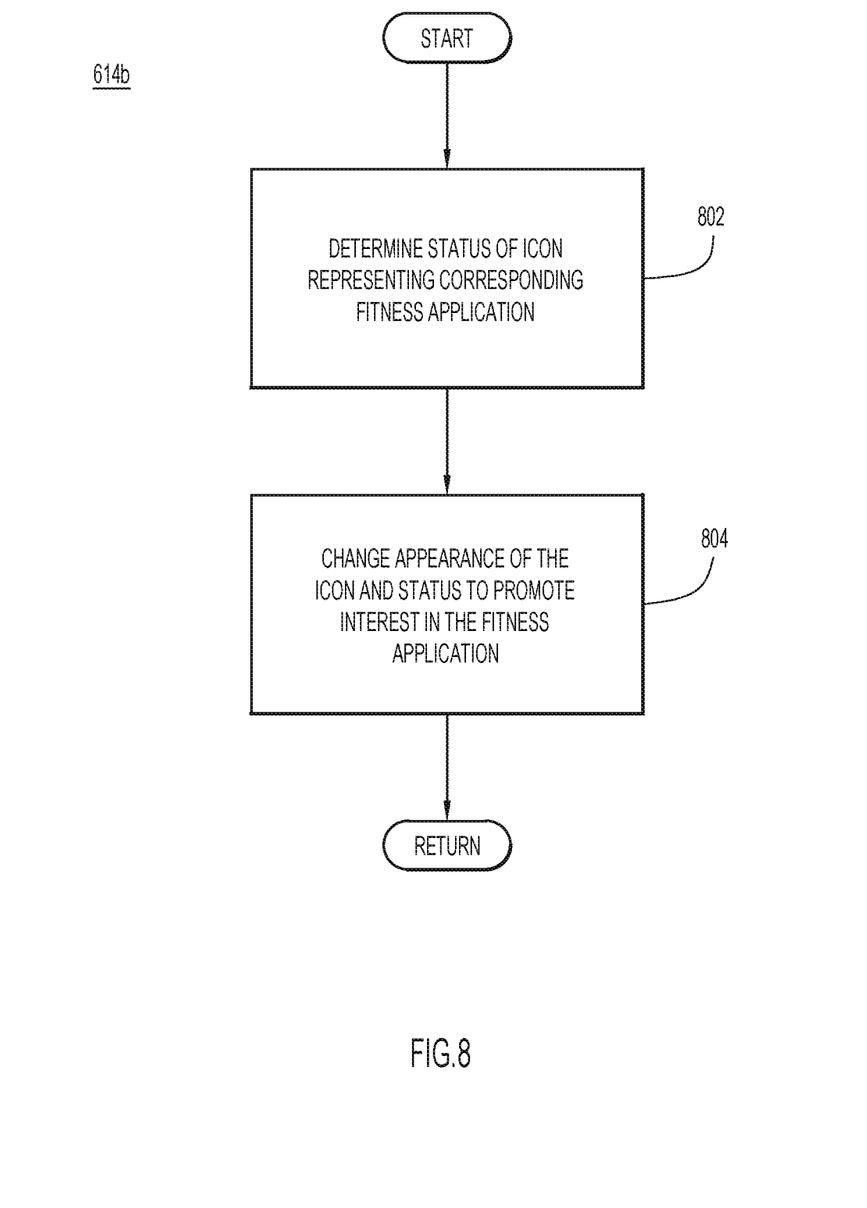
FIG. 8 is a flowchart for explaining an example process for performing the action for inactivity indicated in the flowchart of FIG. 6 according to a second embodiment of the invention.
Figure 10:
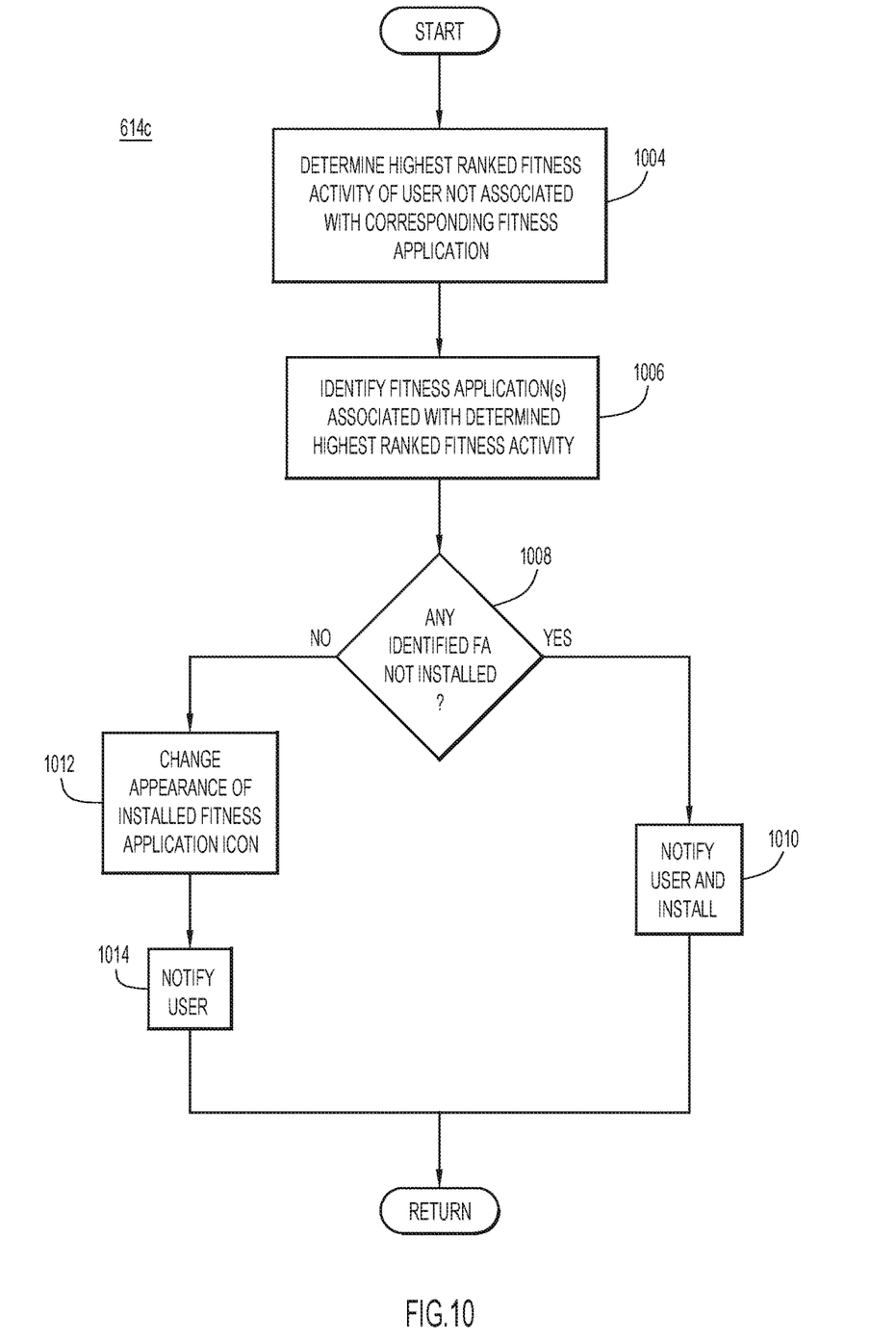
FIG. 10 is a flowchart of example processing, according to an embodiment of the invention, for updating fitness applications on a user device.

If, during act 606, the inactivity timer of the fitness application is determined to be running, then the user's device may determine whether the inactivity timer expired (act 612). If the user's device determines that the inactivity timer did expire, then the user's device may cause an action to be performed (act 614), as described below (FIGS. 7, 8 and 10). Otherwise, the user's device may wait a period of time until monitoring the activity level of the fitness application again (act 618).

If, during act 604, the user's device determines that the activity level of the fitness application is not below the threshold, then the user's device may stop the inactivity timer (act 616) and may wait a period of time before monitoring the activity level of the fitness application again.

FIG. 7 is a flowchart of an example process 614*a* for implementing act 614 of FIG. 6. The process may begin with server 106 monitoring network sites such as, for example, social networking sites, for information exchanged regarding any fitness activities (act 702). Server 106 may then rank the fitness activities based on how frequently each activity is mentioned in the information exchanges (act 704). Server 106 may then categorize and tag the fitness activities by, for example, referring to a table of tags and corresponding fitness activities as mentioned previously (act 706).

Server 106 may then send a message to the user's device to cause the user's device to prompt the user to select one of a top N ranked fitness activities (act 708), where N may be 1, 5, 10, or another suitable number. The user may select one of the top N ranked fitness activities via a user interface of the user's device. The users device may provide an indication of the selected one of the top N ranked fitness activities to server 106. At act 710, server 106 determines whether an indication of the selected one of the top N ranked fitness activities was received from the user's device (act 710). If the received indication indicates no selection, then the process is completed. Otherwise, server 106 may identify a corresponding fitness application for monitoring the selected one of the top N fitness activities by, for example, searching descriptions of fitness applications at known fitness application developer websites and/or fitness application seller websites (act 712) and may install the identified fitness application on the user's device (if not already installed), assuming that the user has given permission for the installing of the identified fitness application (act 714). The process may then be completed.

In a variation of process 614a, server 106 may determine whether a number of identified fitness applications for measuring the selected fitness activity is below a threshold and, if so, server 106 may send a notification to an application developer website promoting development of fitness applications to monitor the selected fitness activity (See acts 410-414; FIG. 4).

FIG. 8 is a flowchart of a process 614b for a second implementation of act 614 of FIG. 6. The process may begin with the user's device determining a status of an icon representing a fitness application corresponding to the fitness activity having the activity level below the inactivity threshold (act 802).

The icon may have a status corresponding to any one of a number of status levels, each of which may have an associated icon appearance. As an example only, the status levels may include level 0, level 1, level 2, level 3, etc., where level 0 indicates that the fitness application has been used during a most recent single period of time, level 1 indicates no use of the fitness application for a single period of time, level 2 indicates no use of the fitness application for two periods of time, level 3 indicates no use of the fitness application for three periods of time, etc. A period of time may be one week, two weeks, one month, or another suitable period of time. Respective icon appearances associated with corresponding status levels may be changed such that, for example, as a level number of a current status increases, a corresponding icon appearance is more likely to attract an attention of the user.

During act 804, the appearance of the icon of the fitness application is changed by the user's device to correspond to the determined status and to promote interest in the fitness application (act 804). Thus, for example, if the status of an icon is determined to be level 0 during act 802, during act 804 the user's device may change the status of the icon to level 1 and may change the appearance of the icon accordingly.

In some embodiments, one way to promote interest in the fitness application and to attract attention of the user may be to vary use of bright colors for the icon such that, as a level number of the status of the icon increases, the use of bright colors for the icon increases. In an alternative embodiment, the icon may be made to blink and as a level number of the status increases, the icon may be made to blink at a faster rate. In other implementations, the appearance of an icon may be varied in a different way with respect to its corresponding status.

Figure 9:
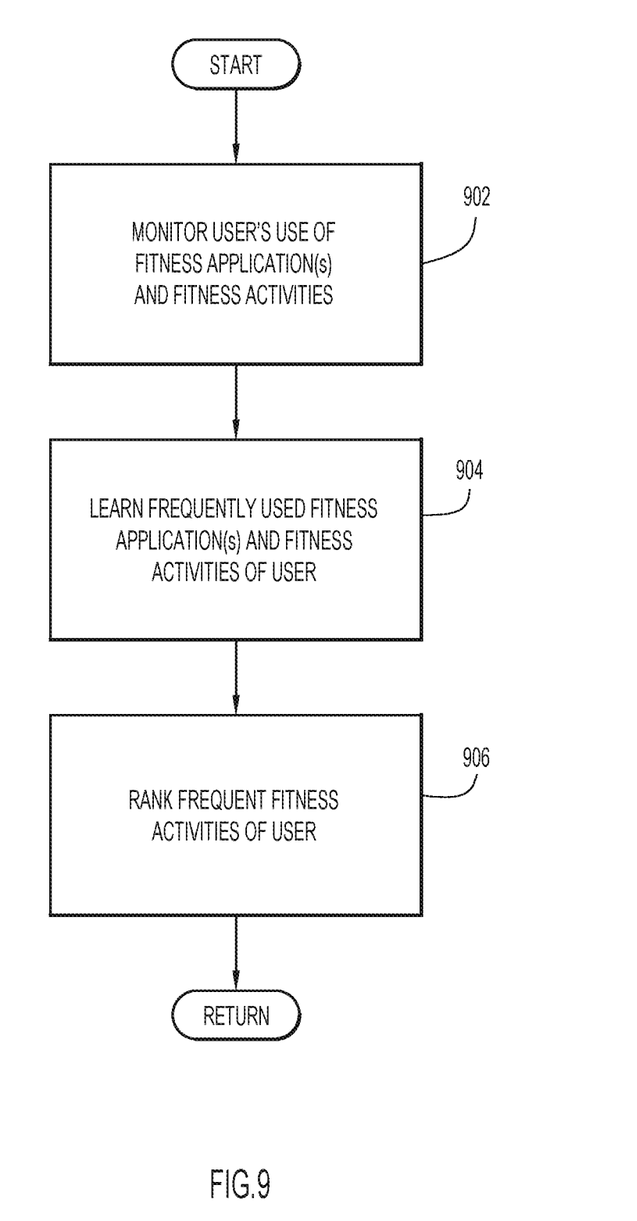
FIG. 9 is a flowchart of example processing, according to an embodiment of the invention, for ranking frequently used fitness applications and corresponding fitness activities of a user.

An embodiment of the invention may use machine learning to learn frequently used fitness applications and corresponding fitness activities of a user. FIG. 9 is a flowchart of an example process that may be performed by a user's device in such embodiments.

The process may begin with the users device monitoring the user's use of fitness applications and corresponding fitness activities (act 902). Based on the monitoring, the user's device may learn the frequently used fitness applications and fitness activities of the user (act 904) and may rank the frequently used fitness activities of the user based on frequency of use of a corresponding fitness application by the user (act 906).

According to some embodiments, the process illustrated by FIG. 6 may be performed in a same embodiment as the process of FIG. 9, which ranks the frequent fitness activities of a user. FIG. 10 illustrates an example process 614c for implementing act 614 of FIG. 6, when the user's device determines that an activity level with respect to a fitness activity has been inactive for at least a given period of time. The process may begin by determining, with respect to the user, a highest ranked user fitness activity not associated with a fitness application corresponding to the fitness activity determined to be inactive (see FIGS. 6 and 9) (act 1004). The user's device may then request server 106 to identify one or more fitness applications associated with the determined highest ranked user fitness activity (act 1006). Server 106 may search for fitness applications corresponding to the fitness activity The user's device may then identify, from the received identified one or more fitness applications, whether any of the identified one or more fitness applications are not installed on the user's device (act 1008). In this embodiment, preference is given to uninstalled fitness applications based on an assumption that having the user try a new fitness application is more likely to interest the user then suggesting that the user reuse a previously used fitness application.

If, during act 1008, the user's device determines that at least one of the identified fitness applications is not installed on the user's device, then the user's device may display a notification to the user suggesting to the user to try one of the identified fitness applications that is not installed on the user's device and requests the user's permission to install the one of the identified fitness applications. The user's device then may install the one of the identified fitness applications assuming that the user gives permission to install the one of the identified fitness applications (act 1010). The process may then be completed.

If, during act 1008, the user's device determines that all of the identified fitness applications are installed on the user's device, then the user's device may change an appearance of an icon representing one of the identified fitness applications to attract an attention of the user (act 1012) and may notify the user to suggest that the user use the one of the identified fitness applications (act 1014). The appearance of the icon representing the one of the identified fitness applications may be changed to highlight the icon or cause the icon to blink. In other implementations, the appearance of the icon may be changed in other ways to attract the attention of the user. The process may then be completed.

In variations of the above-mentioned embodiments, server 106 may obtain a version of a fitness application to promote. The version of the fitness application may have limited functionality. Server 106 may send a notification to a user's device asking whether the user would like to sample the fitness application. If the user indicates, via the user's device, a desire to sample the fitness application, server 106 may install the version of the fitness application with limited functionality on the user's device. As an alternative, the version of the fitness application may have full functionality, but may only be permitted to execute on the user's device for a limited period of time such as, for example, one week, one day, or another period of time, after which the user must purchase the fitness application to continue using the fitness application.

In other variations of the embodiments, after a top ranked number of fitness activities and corresponding fitness applications is determined by server 106 based on monitoring social networking sites, server 106 may provide information regarding the corresponding fitness applications to the user's device. The user's device may then alter an appearance of icons of the corresponding fitness applications indicating that the corresponding fitness applications can monitor at least one of the top ranked number of fitness activities.

It will be appreciated that the embodiments described above and illustrated in the drawings represent only a few of the many ways of implementing various embodiments.

The environment of the present invention embodiments may include any number of computer or other processing systems and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various computing systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures to store information. The database system may be included within or coupled to server and/or client systems. The database systems and/or storage structures may be remote from or local to a computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figs. illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figs. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method of monitoring user activity, wherein the method is performed by at least one computing device and comprises:
monitoring, by the at least one computing device, information exchanged via at least one network site for any mention of one or more fitness activities;
searching, by the at least one computing device, at least one from a group of websites of known fitness application developers and websites of known application sellers to identify a respective fitness application for at least some of the one or more mentioned fitness activities, wherein each of the respective fitness applications monitors user performance of a corresponding fitness activity; and
installing, by the at least one computing device, the identified respective fitness application for each of the at least some of the one or more mentioned fitness activities on a wearable fitness tracking device of a user coupled to the at least one computing device over a network to configure the wearable fitness tracking device to monitor user performance of the corresponding fitness activity.

2. The method of claim 1, wherein the at least one network site further comprises at least one social network site.

3. The method of claim 1, wherein:
the monitoring further comprises counting, by the at least one computing device, a frequency at which each of the one or more fitness activities is mentioned in the monitored information exchanged; and
the method further comprises:
ranking, by the at least one computing device, the one or more mentioned fitness activities based on the corresponding frequency counted within the monitored information exchanged;
determining a top predetermined number of fitness activities from the ranked one or more fitness activities;
sending a message to the wearable fitness tracking device, the message causing the wearable fitness tracking device to prompt the user to select a fitness activity from the top predetermined number of the fitness activities; and
responsive to receiving the selected fitness activity from the wearable fitness tracking device, installing, by the at least one computing device, on the wearable fitness tracking device a corresponding identified fitness application for the selected fitness activity.

4. The method of claim 1, further comprising:
tagging, by the at least one computing device, the one or more mentioned fitness activities based on one or more from a group of a physical intensity of a fitness activity and a category of a fitness activity.

5. The method of claim 1, further comprising:
in response to identifying a quantity of fitness applications below a threshold for at least one of the one or more fitness activities, transmitting a notification to an application developer website regarding development of fitness applications for the at least one of the one or more fitness activities.

6. The method of claim 1, further comprising:
receiving, by the at least one computing device, a web address of a fitness video
analyzing, by the at least one computing device, content at the web address to determine a fitness activity associated with the fitness video;
searching, by the at least one computing device, the at least one from the group of websites of known fitness application developers and the websites of known application sellers to identify a fitness application for the fitness activity associated with the video; and
installing, by the at least one computing device, on the wearable fitness tracking device the identified fitness application for the fitness activity associated with the video.

7. The method of claim 1, further comprising:
altering an identified fitness application based on one or more from a group of inactivity of a user and at least one social network of a user.

8. A system for monitoring user activity comprising:
at least one computing device including:
at least one processor; and
at least one memory connected to the at least one processor, the at least one processor being configured to perform:
monitoring information exchanged via at least one network site for any mention of one or more fitness activities;
searching at least one from a group of websites of known fitness application developers and websites of known application sellers to identify a respective fitness application for at least some of the one or more mentioned fitness activities, wherein each of the respective fitness applications monitors user performance of a corresponding fitness activity; and
installing the identified respective fitness application for each of the at least some of the one or more mentioned fitness activities on a wearable fitness tracking device of a user coupled to the at least one computing device over a network to configure the wearable fitness tracking device to monitor user performance of the corresponding fitness activity.

9. The system of claim 8, wherein:
the monitoring further comprises counting a frequency at which each of the one or more fitness activities is mentioned in the monitored information exchanged; and
the at least one processor is further configured to perform:
ranking the one or more mentioned fitness activities based on the corresponding frequency counted within the monitored information exchanged;
determining a top predetermined number of fitness activities from the ranked one or more mentioned fitness activities;
sending a message to the wearable fitness tracking device, the message causing the user wearable fitness tracking device to prompt the user to select a fitness activity from the top predetermined number of the fitness activities; and
responsive to receiving the selected fitness activity from the wearable fitness tracking device, installing on the wearable fitness tracking device a corresponding identified fitness application for the selected fitness activity.

10. The system of claim 8, wherein the at least one network site further comprises at least one social network site.

11. The system of claim 8, wherein the at least one processor is further configured to perform:
tagging the one or more mentioned fitness activities based on one or more from a group of a physical intensity of a fitness activity and a category of a fitness activity.

12. The system of claim 8, wherein the at least one processor is further configured to perform:
receiving information from a user pertaining to at least one fitness activity, one of the at least one fitness activity being an outdoor activity and the information including a weather restriction regarding performance of the outdoor activity;
monitoring a local weather condition;
scheduling a first fitness application to monitor the user performance of the outdoor activity when the monitored local weather condition complies with the weather restriction regarding the performance of the outdoor activity; and
scheduling a second fitness application to monitor the user performance of a corresponding indoor second fitness activity when the monitored local weather condition does not comply with the weather restriction for performance of the outdoor activity.

13. The system of claim 10, wherein the at least one processor is further configured to perform:
monitoring an activity level associated with an installed fitness application;
when the monitored activity level is below an activity threshold for at least a preset time interval, suggesting installing at least one fitness application for monitoring at least one fitness activity corresponding to at least one of the top predetermined number of fitness activities.

14. The system of claim 8, wherein the at least one processor is further configured to perform:
monitoring an activity level associated with an installed fitness application;
when the monitored activity level is below an activity threshold for at least a preset time interval:
altering an icon corresponding to one of the identified fitness applications.

15. A computer program product comprising at least one computer readable storage medium having computer readable program code embodied therewith for execution on at least one processor, the computer readable program code being configured to be executed by the at least one processor to perform:
monitoring information exchanged via at least one network site for any mention of one or more fitness activities;
searching at least one from a group of websites of known fitness application developers and websites of known application sellers to identify a respective fitness application for at least some of the one or more mentioned fitness activities, wherein each of the respective fitness applications monitors user performance of a corresponding fitness activity; and
installing the identified respective fitness application for each of the at least some of the one or more mentioned fitness activities on a wearable fitness tracking device of a user coupled to the at least one processor over a network to configure the wearable fitness tracking device to monitor user performance of the corresponding fitness activity.

16. The computer program product of claim 15, wherein the at least one network site further comprises at least one social network site.

17. The computer program product of claim 15, wherein:
the monitoring further comprises counting a frequency at which each of the one or more fitness activities is mentioned in the monitored information exchanged; and
the computer readable program code is further configured to be executed by the at least one processor to perform:
ranking the one or more mentioned fitness activities based on the corresponding frequency counted within the monitored information exchanged;
determining a top predetermined number of fitness activities from the ranked one or more fitness activities;
sending a message to the wearable fitness tracking device, the message causing the wearable fitness tracking device to prompt the user to select a fitness activity from the top predetermined number of the fitness activities; and
responsive to receiving the selected fitness activity from the wearable fitness tracking device, installing on the wearable fitness tracking device a corresponding identified fitness application for the selected fitness activity.

18. The computer program product of claim 15, wherein the computer readable program code is further configured to be executed by the at least one processor to perform:
tagging the one or more mentioned fitness activities based on one or more from a group of a physical intensity of a fitness activity and a category of a fitness activity.

19. The computer program product of claim 15, wherein the computer readable program code is further configured to be executed by the at least one processor to perform:
receiving a web address of a fitness video;
analyzing content at the web address to determine a fitness activity associated with the video;
searching the at least one from the group of websites of known fitness application developers and the websites of known application sellers to identify a fitness application for the fitness activity associated with the video; and
installing on the wearable fitness tracking device the identified fitness application for the fitness activity associated with the video.

20. The computer program product of claim 15, wherein the computer readable program code is configured to be executed by the at least one processor to perform:
sending a message to the wearable fitness tracking device to cause the wearable fitness tracking device to prompt a user to select a sample fitness application, the sample fitness application having either a limited functionality with respect to a corresponding fully functional fitness application or having full functionality and being operational for a limited period of time;
receiving a selection of the sample fitness application from the wearable fitness tracking device; and
responsive to receiving the selection of the sample fitness application, installing the sample fitness application on the wearable fitness tracking device to monitor user performance of a corresponding fitness activity.

* * * * *